United States Patent [19]

Isono et al.

[11] Patent Number: 4,517,178

[45] Date of Patent: May 14, 1985

[54] NOVEL ANTIBIOTIC 76-11, PROCESS FOR THE PRODUCTION THEREOF, ANTICOCCIDIOSIS AGENT AND DOMESTIC ANIMALS GROWTH ACCELERATOR COMPRISING THE SAME AS AN EFFECTIVE INGREDIENT

[75] Inventors: Kiyoshi Isono, Niiza; Goto Nakamura, Urawa; Shigeo Fujita, Tokyo, all of Japan

[73] Assignees: Rikagaku Kenkyusho, Wako; Kaken Kagaku Kabushiki Kiasha, Tokyo, both of Japan

[21] Appl. No.: 502,533

[22] Filed: Jun. 13, 1983

Related U.S. Application Data

[63] Continuation-in-part of Ser. No. 353,641, Mar. 1, 1982, abandoned.

[30] Foreign Application Priority Data

Aug. 4, 1981 [JP] Japan ................................ 56-122210

Dec. 22, 1981 [JP] Japan ................................ 56-207464

[51] Int. Cl.³ ........................ A61K 35/74; C12P 1/06; C12P 1/04
[52] U.S. Cl. .................................... 424/122; 435/169; 435/170
[58] Field of Search ................. 435/169, 170; 424/122

Primary Examiner—Jerome D. Goldberg
Attorney, Agent, or Firm—Bucknam and Archer

[57] ABSTRACT

This invention relates to a novel antibiotic 76-11; process for the production thereof which comprises culturing an antibiotic 76-11 producing microorganism belonging to the genus Actinomadura to separate and collect the antibiotic; an anticoccidiosis agent comprising the antibiotic as an effective ingredient; and a growth accelerating and feed efficiency increasing agent for domestic animals and fowls comprising the antibiotic as an effective ingredient.

7 Claims, 3 Drawing Figures ial, this invention relates to a novel antibiotic 76-11,

NOVEL ANTIBIOTIC 76-11, PROCESS FOR THE PRODUCTION THEREOF, ANTICOCCIDIOSIS AGENT AND DOMESTIC ANIMALS GROWTH ACCELERATOR COMPRISING THE SAME AS AN EFFECTIVE INGREDIENT

This application is a continuation-in-part of application Ser. No. 353,641, filed Mar. 1, 1982, now abandoned.

BACKGROUND OF THE INVENTION

Field of the Invention

This invention relates to an antibiotic, a process for the production thereof, an anticoccidiosis agent and a growth accelerating and feed efficiency increasing agent for domestic animals and fowls comprising the antibiotic as an effective ingredient and more particularly, this invention relates to a novel antibiotic 76-11, process for the production thereof which comprises culturing an antibiotic 76-11 producing microorganism belonging to the genus Actinomadura to separate and collect the antibiotic; an anticoccidiosis agent comprising the antibiotic as an effective ingredient; a growth accelerating and feed efficiency increasing agent for domestic animals and fowls comprising the antibiotic as an effective ingredient; a method for preventing and treating coccidiosis; a method for accelerating the growth of domestic animals and increasing feed efficiency; and feed for domestic animals and fowls comprising the antibiotic.

The inventors of the present invention, for the purpose of searching a new useful antibiotic, isolated a microorganism from soil collected in various places and studied an antibiotic produced by the microorganism. As a result, the inventors found that a new antibiotic 76-11 which has never been known in any published literature, was produced by a microorganism belonging to the genus Actinomadura and was accumulated in the cell and culture medium.

On the other hand, a coccidiosis is an infectious disease of domestic fowls caused by Protozoa belonging to the genus Eimeria and, causes in fowls scours and poor intake of nutrition and finally bring them death.

Oocyst which is the first generation of Protozoa is excreted with droppings, forms spores and infects fowls one after another. Typical Protozoa described above includes *Eimeria tenella, Eimeria acervulina, Eimeria necatrix, Eimeria brunetti, Eimeria maxima,* and so on. Fowls infected with Protozoa lose their commercial value. Therefore, the prevention of coccidiosis is a matter of industrial importance. Accordingly, various kinds of preventive and curative means have heretofore been proposed and widely studied. Examples of the proposed agent include arsenic, nitrofuran, or bisphenol compounds, sulfa drugs, thiazine, quinoline, pyridine or guanidine derivatives, and so on. However, these agents are not effective enough and further, some new protozoans having a resistance to these agents appear. Accordingly, there has been a need of a new effective agent.

Under these conditions, the inventors have conducted a study of a medical agent effective against coccidiosis of fowls and found that the antibiotic 76-11 is extremely effective against coccidiosis of fowls.

Some antibiotics have been added to feed in order to accelerate the growth and to increase egg-laying of domestic animals and fowls. However, due to the application to animals of common antibiotics to a man and animals, resistant strains appear, which has caused some fear of harmful effect on medical cure of humans. Further, a man also have another fear of intake the antibiotic applied to and accumulated in the animal body when eating the meat or the products.

The inventors studied growth accelerating agents having none of the disadvantages described above and found that the administration of the antibiotic 76-11 to domestic animals or fowls accelerates the formation of propionic acid in digestive organs and inhibits the increase in viscosity of rumen liquid. On the other hand, it is known that propionic acid is superior to acetic or butyric acids in the coefficient of energy utilization of volatile fatty acid in a living animal body. From the facts described above, the inventors demonstrated that the antibiotic 76-11 would be an excellent agent being capable of accelerating the growth of domestic animals and fowls and increasing feed efficiency thereof.

The inventors have now accomplished the present invention based on the above discoveries.

SUMMARY OF THE INVENTION

An object of this invention is to provide a new antibiotic 76-11.

Another object of this invention is to provide a method for producing the antibiotic 76-11.

A further object of this invention is to provide an effective agent against coccidiosis of domestic fowls.

Another object of this invention is to provide an excellent agent being capable of accelerating the growth of domestic animals and fowls and increasing feed efficiency thereof.

Still a further object of this invention is to provide a method for preventing and treating coccidiosis of domestic fowls.

A further object of this invention is to provide a method for accelerating the growth of domestic animals and fowls and increasing feed efficiency thereof.

The other object of this invention is to provide a feed for fowls effective for prevention and treatment of coccidiosis.

A further object of this invention is to provide feed for domestic animals and fowls, being capable of accelerating the growth and increasing feed efficiency.

These objects of this invention can be achieved by the new antibiotic 76-11 which is produced by culturing a microorganism being capable of producing the antibiotic 76-11, such as the genus Actinomadura Sp. 76-11 (hereinafter referred to as "Sp. 76-11") and isolating the antibiotic 76-11 from the culture liquid.

DETAILED DESCRIPTION OF THE INVENTION

Figure 1:
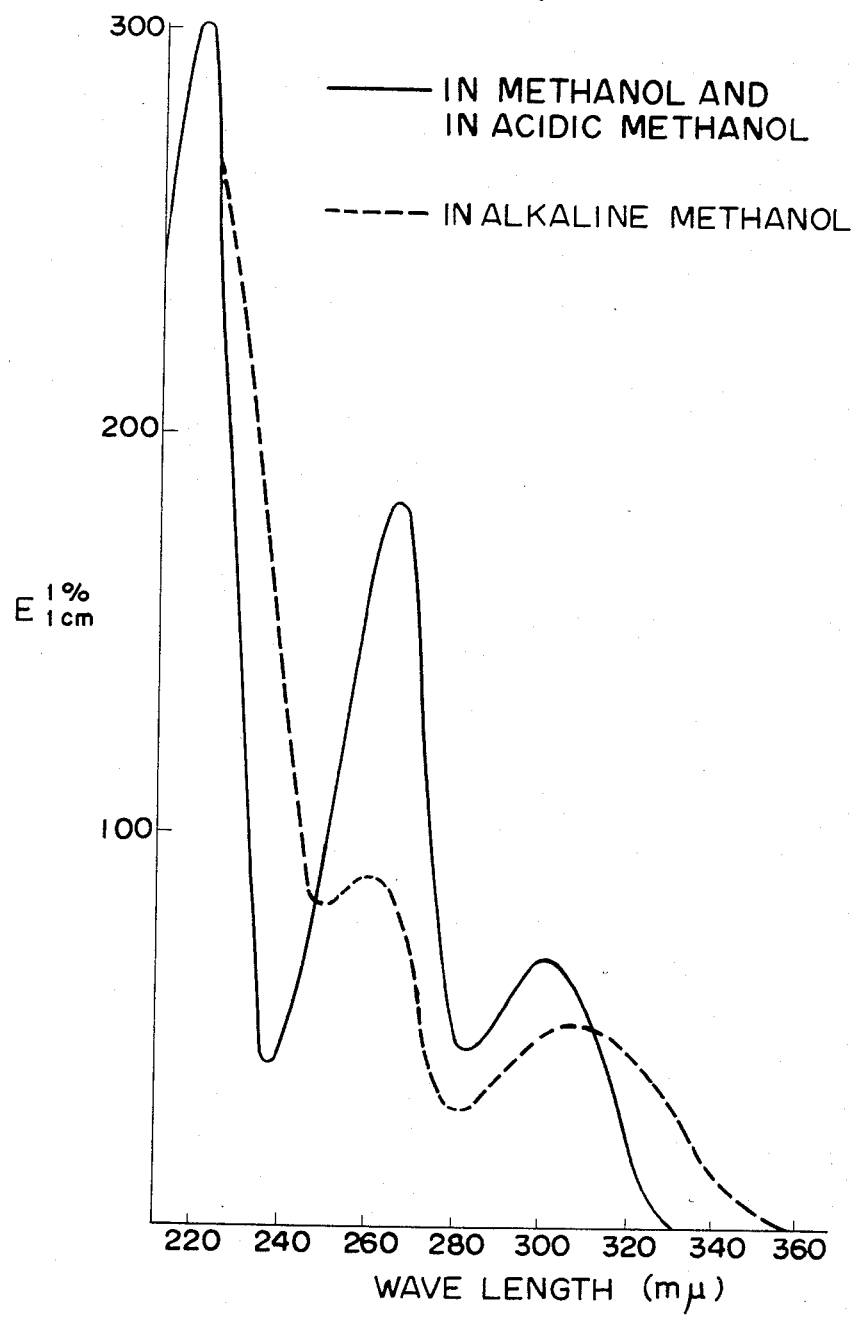
FIG. 1 shows an ultraviolet absorption spectrum of the antibiotic 76-11 (free acid) of the invention.
Figure 2:
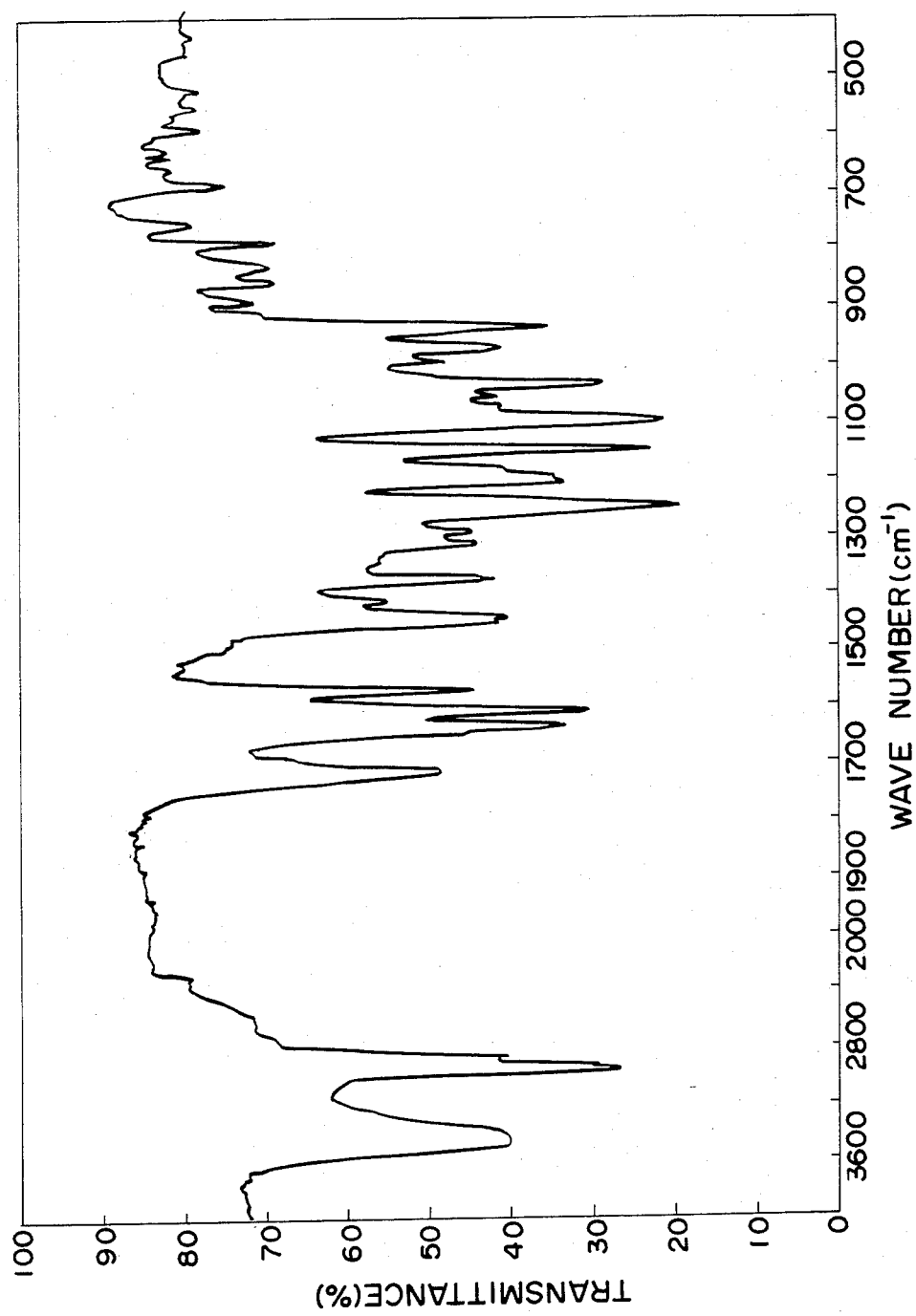
FIGS. 2 and 3 show infrared absorption spectra of the antibiotic 76-11 in the form of Na salt and free acid (in KBr plate), respectively.
Figure 3:
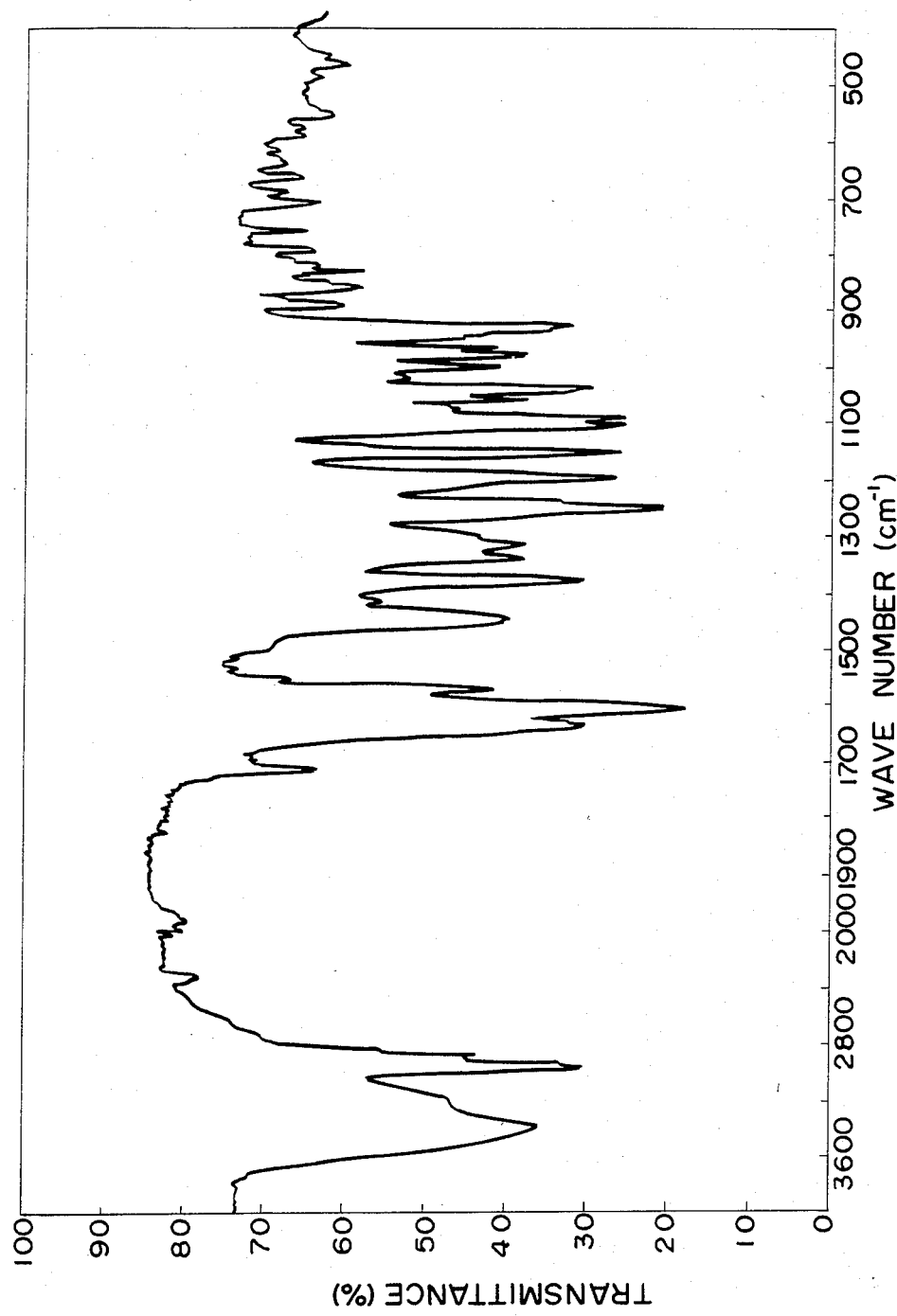

The new antibiotic 76-11 and process for the production thereof will now be described in detail.

The microorganisms used in the process of this invention belong to the genus Actinomadura and are capable of producing the antibiotic 76-11. One example of the microorganisms in Sp. 76-11 which belongs to the genus Actinomadura and has the following microbiological properties. Not only natural and artificial mutants of Sp. 76-11 but also all the species belonging to the genus Actinomadura and being capable of producing the antibiotic 76-11 may be used in this invention. The Sp. 76-11 was deposited with the Fermentation Research Institute, Agency of Industrial Science and Technology, Ministry of International Trade and Industry, Japan, International Depositary Authority (hereinafter referred to as "FERM" under the accession number of FERM BP-83), and is on deposit with FERM in an unrestricted deposit permitting the full access to the culture. The applicants will irrevocably remove all restrictions on the availability on the granting of a patent and will maintain the deposition of FERM BP-83 in the unrestricted form until the end of the duration of a patent granted on this application if a patent is granted on this application, will maintain the culture and thus said microorganism strain will be available to any third party at any time until the end of the duration of the patent granted on this application. Sp. 76-11 has the following microbiological properties.

The properties of Sp. 76-11 on various culture media were observed 20 to 30 days after the inoculation. Color tones described in parenthesis are based on the Description Color Name Dictionary.

(I) Morphology

Sp. 76-11 grows on oatmeal agar and malto extract—yeast extract agar culture media but does not or hardly grow on the other ones and therefore, the morphology on oatmeal agar, malto ertract-yeast extract agar, 3% oatmeal liquid culture media was observed. The results are as follows:

(i) Substrate mycelia

Substrate mycelia stretch and ramify on both the agar and the liquid culture media. After a long period of culturing, substrate mycelia divide to form elliptical spores the size of which is $0.8-1.2 \times 1.5-1.7\mu$. Aerial mycelia are not formed on various culture media but, when cultured on oatmeal agar culture medium at 33° C. for more than twenty days, white, thin aerial mycelia are sometimes formed, which are bent and string-like or fasciculate, have branches a little and form no spores.

(ii) Aerial mycelia

Not formed on various culture media but sometimes formed on oatmeal agar culture medium when cultured for more than 30 days. The aerial mycelia formed are irregularly bent. No spores are observed under an electron microscope.

(II) Cell composition

Sp. 76-11 was cultured on the culture medium comprising 1% glucose, 1% yeast extract and 0.1% oatmeal at 33° C. for 7 days with shaking. Cells were collected and washed to give a sample for analysis of cell composition. Diamino pimelic acid and sugar composition were analyzed. Meso type of diamino pimelic acid, galactose and madurose were detected.

(III) Growth on various culture media (i) Sucrose nitrate agar culture (Czapeck's agar culture):

Growth: Very poor. Slight growth observed after 30 days of culturing. The colony is transparent. The surface is light brown (2 ea) and the back is light ivory (2 ca).

Aerial mycelia: Not formed.
Soluble pigment: Not formed.

(ii) Glucose asparagine agar culture:
No growth observed.

(iii) Glycerin asparagine agar culture:
No growth observed.

(iv) Inorganic salt starch agar culture:
Growth: Very poor. Slight growth observed after 30 days. The surface is light yellow brown (3 gc) and the back is yellow brown (3 ie).

Aerial mucelia: Not formed.
Soluble pigment: Not formed.

(v) Tyrosine agar culture:
Growth: Very poor. The surface is light yellow (3 ca) and the back is light ivory (2 ca).

Aerial mycelia: Not formed
Soluble pigment: Not formed.

(vi) Nutrient agar culture:
Growth: Very poor. After 30 days, both the surface and the back are light ivory (2 ca).

Aerial mycelia: Not formed.
Soluble pigment: Not formed.

(vii) Yeast-extract malto-extract agar culture (ISP No. 2):
Growth: Good. The surface is like a furrowed, hard coating, and both the surface and the back are light brown (2 ne), sometimes bluish (10 ie).

Aerial mycelia: Slightly white aerial mycelia are formed at times after a long period of culturing.
Soluble pigment: Not formed.

(viii) Oatmeal agar culture (ISP No. 3):
Growth: Good. The surface is smooth, coating-like and blue-indigo (10 ie) and the back is white, finally blue-indigo (10 ne).

Aerial mycelia: White aerial mycelia are formed at times after 30 days.
Soluble pigment: Not formed.

(ix) Peptone yeast-extract iron agar culture (ISP. No. 6):
No growth is observed.

(x) Skim milk (37° C.)
Growth: Slow. Coagulated and peptonized.

(xi) Glucose peptone gelatin culture (20° C.):
Growth: Very slow. Liquidization is observed.

(IV) Physiological Properties (i) Optimum temperature for growth: 27° to 37° C., most preferably 33° to 37° C.

(ii) Liquidization of gelatin: yes (iii) Hydrolysis of starch: no (iv) Skim milk:
Coagulated and slightly peptonized.

(v) Formation of melanin-like pigment: no (vi) Resistance to acid:
Acid resistant.

(V) Utilization of Various Carbon Sources:

Sp. 76-11 was cultured on Pridham and Gottlieb agar culture (ISP No. 9) (produced by Diffco Co.) containing various sugars but no growth was observed and therefore, the culture medium described above to which 0.1% yeast extract was added, was used instead. The results obtained are as follows:

| L-Arabinose | +++ |
| D-Xylose | +++ |
| D-Glucose | +++ |
| D-Fructose | +++ |
| Sucrose | +++ |
| 1-Inositol | ++ |
| L-Rhamnose | +++ |
| Raffinose | ++ |
| Mannitol | ++++ |

-continued

| Control | ± |
| --- | --- |

Note:
++++: Very good growth.
+++: Good growth
++: Growth
±: Control

Characteristics of Sp. 76-11

In brief, Sp. 76-11 may be characterized by:
(i) Morphology:
Sp. 76-11 does not generally form aerial mycelia but, sometims forms after a long period of culturing. Substrate mycelia are bent, and in the latter period of culturing, divide to form elliptical spores. The mycelia are Gram positive and acid resitant.

(ii) Growth on various media:
Sp. 76-11 does not or hardly grow on all various agar culture media but oatmeal agar and yeast-extract malto-extract agar culture media.

The strain grows best on oatmeal agar culture medium and forms blue-indigo, water insoluble pigment in the cell after 3 to 4 weeks of culturing.

(iii) Physiological Properties:
The strain grows well at 33° to 37° C., liquidizes slightly gelatine, coagurates and peptonizes skim milk, and forms no melanin pigment.

(iv) Utilization of sugar:
The strain utilizes well any of L-arabinose, D-xylose, D-glucose, D-fructose, sucrose, 1-inositol, L-rhamnose, raffinose and mannitol on Pridham Gottlieb agar culture medium to which 0.1% yeast extract was added.

As described above, Sp. 76-11 seems to be a strain belonging to the genus Actinomadura of Actinomycetes from the morphology of spores and mycelia, growth on various media and cell-wall composition. However, comparing the characteristics of Sp. 76-11 with those of strains belonging to the genus Actinomadura, described in Nonomura, H. & Y. Ohara: Distribution of actinomycetes in soil. XI. Some new species of the genus Actinomadura, Lechevalier et al. J. Ferment. Technol. 49:904–912, 1971, Preobrazhenskaya, T. P.; M. A. Sveshnikova & L. P. Terek hova: Key for identification of the species of the Genus Actinomadura. The Biology of the Actinomycetes & Related Organisms 12:30–38, 1977, no strains which produce blue-indigo pigment in cell on oatmeal agar culture medium as Sp. 76-11 does, are described therein. Accordingly, it was concluded that Sp. 76-11 is a new strain belonging to the genus Actinomadura.

In producing the antibiotic 76-11, an antibiotic 76-11-producing microorganism may be cultured according to a conventional method used in the production of antibiotic. The culturing mode is not particularly critical and either liquid culturing or solid culturing may be adopted. In order to perform culturing industrially and advantageously, it is recommended to adopt a method in which a culture medium is inoculated with a spore suspension or culture medium of an antibiotic 76-11-producing microorganism and the culturing is carried out with aeration and agitation.

The nutritive source that is used in the present invention is not particularly critical, but any of nutritive sources customarily used for culturing microorganisms may be used. There may be used starch, dextrin, glycerin, glucose, sucrose, galactose, inositol, mannitol, etc. as carbon sources and oatmeal, yeast, peptone, soybean powder, meat extract, rice bran, wheat bran, urea, corn steep liquor, ammonimum salts, nitrates and the other organic or inorganic nitrogen compounds as nitrogen sources, respectively. If desired, other inorganic salts, such as sodium chloride, phosphates, metal salts of pottassium, calcium, zinc, manganese, iron may be added. Animal, vegetable or mineral oils may also be added to the medium, if needed. The culture conditions such as temperature and time may be suitably selected for the maximum production of the antibiotic 76-11. The culturing is carried out at pH 4 to 9, preferably at around pH 7 at 25° to 35° C., preferably 28° to 33° C. for about 5 to 20 days, preferably about 5 to 11 days. However, it is to be understood that such culture conditions as medium composition, pH, temperature, agitation may suitably be varied to obtain the optimum result according to the kind of strain used and external conditions. After culturing, the culture solution is subjected to, for example, a centrifugation to separate the cells from the solution. The antibiotic 76-11 thus produced can be isolated from the culture medium by any conventional method which is usually used for the isolation of metabolite. For example, a method using solubility difference between the antibiotic 76-11 and impurity, a method using difference of adsorptive affinity between them, or a combination thereof may be used and repeated, if needed. Specifically, the antibiotic 76-11 produced exists both in the culture solution and within the cells, and can be extracted from the culture solution, using ethyl or butyl acetates, chloroform, butanol, or the like, according to a difference in solubility between them. The cells are extracted with water-containing acetone or water-containing methanol, the organic solvent are evaporated under reduced pressure, and the aqueous solution thus obtained is extracted with ethyl acetate or the like. Both extracted solutions are combined and concentrated to give a crude extract of the antibiotic 76-11. As the crude extract contains a great amount of impurity, it is subjected to adsorption chromatography using silica gel, alumina or the like and then purified. For example, the crude extract dissolved in a small amount of benzene is introduced to a silica gel column previously conditioned with benzene. Then, elution is conducted with benzene successively with a mixed solvent of benzene and ethyl acetate in which ethyl acetate content is gradually increased. The eluate is fractionized by a fraction collector. The fractions showing a biological activity are collected and concentrated to give purified powder. For further purification, the similar procedure of silica gel chromatography is repeated. Still further purification is carried out by a preparative thin layer chromatography, if necessary. Concentration under reduced pressure gives a purified product which is then dissolved in a small amount of methanol and is refrigerated, the antibiotic 76-11 is separated out as a colorless crystal. The crystal is separated by filtration and dried to give pure antibiotic 76-11.

The antibiotic 76-11 thus obtained shows the following physicochemical and biological properties.

Physicochemical and Biological Properties of the Antibiotic 76-11

(1) Elemental Analysis:
Free acid: C; 62.61%, H; 8.27%, N; 0%, O: 28.10%.
Na salt: C; 60.57%, H; 8.04%, N; 0%, O: 27.38%.
(2) Molecular Weight:
843 (measured by a titration method)

873 (measured by FD mass spectrum method)

(3) Melting Point:

Free acid: 108°–112° C.

Na salt: 210°–212° C. (Decomposed)

(4) Specific Rotatory Power: $[\alpha]_D^{25} +36.6°$ (C=0.382, in chloroform solution)

(5) Ultraviolet Absorption Spectrum: The maximum absorption bands;

In MeOH and HCl—MeOH:

$\lambda_{max}$ = 217 mµ (E$^{1\%}_{1\ cm}$ 303)

262 mµ (E$^{1\%}_{1\ cm}$ 182)

301 mµ (E$^{1\%}_{1\ cm}$ 68)

In alkaline MeOH:

$\lambda_{max}$ = 260 mµ (E$^{1\%}_{1\ cm}$ 87)

308 mµ (E$^{1\%}_{1\ cm}$ 50)

(6) Infrared Absorption Spectrum:

Main specific absorption bands in KBr plate:

Free acid: 3450, 2960, 1720, 1640, 1610, 1578, 1446, 1380, 1315, 1292, 1250, 1209, 1151, 1100, 1035, 975, 940 cm$^{-1}$.

Na salt: 3390, 2960, 1718, 1640, 1609, 1578, 1450, 1380, 1340, 1316, 1250, 1197, 1152, 1108, 1092, 1060, 1040, 1002, 980, 930 cm$^{-1}$.

(7) Solvent Solubility:

Easily soluble in benzene, chloroform, ethyl acetate and acetone, soluble in methanol, ethanol and dimethylformamide, and hardly soluble in water and hexane.

(8) Coloring Reactions:

Positive to potassium permanganate reaction but negative to periodic acid-benzidine reaction.

(9) Basicity, Acidity or Neutrality:

Acidic substance, pKa' 4.6 (in 66.7% dioxane).

(10) Color:

Colorless crystal.

(11) Antimicrobial Activity:

The minimum concentration for inhibiting growth of various microorganisms on bouillon agar culture medium is as shown below.

| Microorganisms tested | The minimum concentration for inhibiting growth (mcg/ml) |
|---|---|
| *Staphylococcus aureus* 209 P | 0.4 |
| *Staphylococcus aureus* (multi resistant) | 0.4 |
| *Bacillus subtilis* PC 1219 | 0.4 |
| *Bacillus subtilis* H 17 | 0.4 |
| *Bacillus subtilis* M 45 (rec$^-$) | 0.4 |
| Mycobacterium SP 607 | 0.4 |
| Mycobacterium phlei | 0.4 |
| Mycobacterium avium | 0.4 |
| Escherichia coli | >100 |
| Salmonella typhimurium | >100 |

(12) Action against tumor cell:

The antibiotic 76-11 shows an induction of differentiation against Friend leukemia and Myeloid leukemia cells in concentration of 1 to 100 mcg/ml.

(13) Toxicity to mice:

Abdominal administration of 50, 100 and 200 mg/kg of the antibiotic 76-11 in the form of CMC suspension showed no toxicity to mice.

Comparing the physicochemical and biological properties of the antibiotic 76-11 described above with those of known antibiotics, the antibiotic 76-11 seems to be classified in the so-called polyether ionophore antibiotic in that it is an acidic substance and Na salt thereof is soluble in oil; that it shows a strong activity against Gram-positive bacteria and acid-fast bacteria; that it does not contain nitrogen in the molecular constitution; and the like. However, no substances show the same physicochemical properties; especially the specific ultraviolet absorption spectrum bands of the antibiotic 76-11 as described above and therefore, the antibiotic 76-11 was concluded to be a new antibiotic and was so named.

Next, the anticoccidiosis agent of the present invention will be described. In using the antibiotic 76-11 as the anticoccidiosis agent, the antibiotic 76-11 may be administered as it stands or administrated to diseased fowls in the form of a feed additive. Examples of feed material include barley flour, wheat flour, rye flour, corn flour, soybean flour, soybean cake, cole seed cake, rice bran, exoleated bran, white potato powder, sweet potato powder, the other various starches, bean-curds (tofu) bran, yeast, fish meal, fermentation residue, and the like. The antibiotic 76-11 may also be added to some conventional feed additive such as various vitamins, minerals, preservatives, enzyme preparations, proteins, carbohydrates, amino acids, febrifuges, sedative agents, antiphlogistics and microbiocides.

The content of the effective ingredient varies according to the kind, the condition of disease, how old domestic fowls are and generally, is in the range of about 5 to 200 ppm, preferably 10 to 100 ppm.

The present invention provides an excellent anticoccidiosis agent which is extremely effective against anticoccidiosis of domestic fowls and shows no toxicity and no side effect.

Then, a growth accelerating and feed efficiency increasing agent for domestic animals and fowls of the present invention will be described.

The growth accelerating and feed efficiency increasing agent of this invention may be prepared by adding the antibiotic 76-11 to feed or drinking water of domestic animals as it stands or in the form of dispersion or solution in diluent, although the agent may also be used in the form of powder, tablet, capsule, granule or pill which may be prepared by mixing the antibiotic 76-11 with or without physiologically harmless solid or liquid diluent. In adding to feed, a premix previously prepared is preferably used. The premix may be prepared by mixing the purified or crude products or the cells containing the effective ingredient with physiologically acceptable, solid or liquid carrier. Examples of solid carrier include wheat flour, soybean flour, rice bran, corn flour, starch, glucose, yeast, fish meal, talc, diatomaceous earth, etc. and examples of liquid carrier include physiologic saline, distilled water, physiologically acceptable organic solvents, etc.

Other appropriate auxiliary or additive such as emulsifying, dispersing, suspending, wetting, concentrating or gelatinizing agents, microbicides, preservatives, enzyme preparations, antibiotics, lactobacilli formulations may be mixed with the agent of this invention.

The content of the effective ingredient in the premix may appropriately be varied according to the kind of domestic animals or fowls.

The concentration of the antibiotic 76-11 in the growth accelerating and feed efficiency increasing agent of the present invention may be changed according to the kind, age and the like. For example, domestic fowls such as chicken, quail, turkey, guinea fowl, duck, goose, etc. are administered as feed which contains the antibiotic 76-11 in the amount of 5 to 200 ppm, preferably 10 to 100 ppm. Feed containing effective ingredient may be used in the amount of 5 to 200 ppm, preferably 10 to 100 ppm for a pig, a rabbit, etc. and 1 to 100 ppm, preferably 2 to 50 ppm for ruminant such as a cattle, a sheep, a goat, etc.

The antibiotic 76-11 of this invention has a low toxicity and an advantage that the administration of the antibiotic 76-11 combined with the other antibiotic to domestic animals or fowls shows substantially no side effects. The administration of polyether antibiotics such as Salinomycin and Monencin in an usual dosage, combined with triacetyl Oleandmycin or Pleuromutilin fumarate in an usual dosage to domestic animals or fowls generally bring them about temporary anorexia or inappetence, hindlegs paralysis and the like and therefore, it should have been heretofore avoided to administer the polyether antibiotic simultaneously with or near the administration of the latter substances. On the contrary, the antibiotic 76-11 does not cause these effects but is an excellent agent which is capable of achieving both the growth acceleration and the increase in feed efficiency of domestic animals and fowls.

The administration of the agent of this invention to domestic animals and fowls accelerates the formation of propionic acid in digestive organs thereof and inhibits the increase in viscosity of rumen liquid, which results not only in the prevention of dysentery, bloat and ketosis of the animals, but also the acceleration of healthy growth of the animals and fowls and the increase in feed efficiency.

In the anticoccidiosis agent and the growth accelerating and feed efficiency increasing agent of the present invention, the effective ingredient or the antibiotic 76-11 may be used in the form of: the purified or crude products; the cells containing the antibiotic 76-11; a physiologically acceptable metal salt (such as sodium, calcium, etc.), an organic acid ester (such as propionic acid ester, valeric acid ester, etc). or a metal complex (such as zinc complex).

The present invention will now be described in details with reference to the following Examples and Test Examples, which do not limit the present invention.

Except for being specified, "%" and "parts" mean "% by weight" and "parts by weight" respectively in the specification and claims.

The following Example shows a process for producing the antibiotic 76-11.

EXAMPLE 1

Production of the antibiotic 76-11

The above-mentioned Sp. 76-11 (FERM BP-83) previously cultured in the slant culture was inoculated to a culture medium comprising 3% oatmeal, 1.5% glycerin and 0.5% meat extract (pH: around 6.5) and cultured at 28° C. for 11 days with shaking. Every 3 ml of the culture solution was inoculated to a fresh culture medium containing the same constituents and cultured further for 7 days.

140 Ml of the culture solution thus obtained was inoculated to 18 l of a culture medium comprising the same constituents in jar fermenter and cultivated at 28° C. for 210 hours with aeration of 18 l/min and agitation of 330 rpm.

After culturing, 400 g of diatomaceous earth (Radiolite 700) was added to the culture solution and then the solution was subjected to a centrifugal filtration. The supernatant obtained (14 l, pH 7.8) was extracted twice with 8 l and 5 l of ethylacetate respectively. On the other hand, the cells was extracted twice with 9 l and 6 l of acetone respectively. The extracted solution was concentrated in vacuo to give 2 l of an aqueous solution (pH 8) which was then extracted twice with each one l of ethylacetate. The latter ethylacetate extracted solution was combined with the former one from the supernatant and concentrated in vacuo. The residue thus obtained was dissolved in a small amount of benzene, which was introduced to a silica gel column ($\phi 3$ cm $\times$ 50 cm) previously conditioned with benzene. Elution was carried out with 2 l of benzene, in turn, 1 l of benzene-ethylacetate (5:1 (v/v)), 1 l of benzene-ethylacetate (1:1 (v/v)). Active fractions were eluted with benzene-ethylacetate (1:1 (v/v)), colleted, concentrated in vacuo and treated with methanol to give about one gram of crude crystal. Several recrystalizations from methanol gave 400 mg pure crystal of sodium salt of the antibiotic 76-11.

Next, a test Example of the anticoccidiosis agent of this invention is shown.

TEST EXAMPLE 1

Anticoccidiosis agent

Agents tested:

The effective ingredients used in this test were uniformly blended to obtain a given concentration with anticoccidiosis agent free perfect combination feed for chick (produced by Oriental Yeast Co., the formulation of which is shown in Table 1). The feeds thus obtained were freely taken by chickens from 2 days before the infection of oocyst to the end of the test (8 days after the infection). Salinomycin was used as control.

TABLE 1

|  | % |
|---|---|
| Corn | 61.2 |
| Wheat flour | 5.13 |
| Soybean oil | 3.07 |
| Soybean meal | 15.4 |
| Fish meal | 10.3 |
| Lucerne meal | 3.07 |
| Calcium, carbonate | 0.3 |
| Salt (NaCl) | 0.5 |
| Vitamine mix | 1.03 |

Chickens used:

Chickens used in this test were healthy cocks of egg-laying fowl (Shaver Starcross) which were 7 days-old (9 days-old when infected) and had been bred under the conditions of perfect prevention of coccidiosis infection. Every group had five chickens. Oocyst inoculated and the quantity of inoculation:

The oocyst used for the infection was a sensitive strain of *Eimeria tenella*. Every chicken was inoculated to the crop with full grown oocysts ($5 \times 10^4$), orally using metal sonde.

Judgement of effect:

The effect of the agents was determined by the anticoccidiosis index (ACI) which was calculated by the following formula:

ACI=(Relative Increase in Weight+Survival Rate)−(Oocyst Value+Disease Value), (i) Relative Increase in Weight Weight of chickens tested was measured at the start of the test (2 days before the inoculation or −2 day), the inoculation (0 day), 2, 4, 5, 6, 7 and 8 days after inoculation. At the end of the test, the increase in weight of each test group was measured and relative increase in weight was calculated based on weight of the control group (100) which were bred with the anticoccidiosis agent free feed and not inoculated.

(iii) Oocyst Value

The number of oocyst in the caecum was counted on 8 days after the inoculation by homogenizing the intestinal canal. The oocyst value was defined as follows:

| The number of oocyst found in the intestinal canal | The oocyst value |
|---|---|
| $0.0–0.1 \times 10^6$ | 0 |
| $0.1–1.0 \times 10^6$ | 1 |
| $1.0–5.0 \times 10^6$ | 10 |
| $5.0–11.0 \times 10^6$ | 20 |
| $>11.0 \times 10^6$ | 40 |

(iii) Disease index of the intestinal canal

The chickens tested were anatomized at the end of the test (8 days after the inoculation) and the intestinal canal was examined with the naked eye to determine the disease index. The disease index was defined as follows and the disease value was defined ten times as many as the value of the disease index.

0, (−) . . . The caecum is quite normal. If bleeding spot is found, (−) is changed to (+).

1, (+) . . . The caecum is normal in shape. The content therein is slightly fluid and yellowish. Slight swelling is found partly on a mucous membrane of the caecum which becomes whitish.

2, (++) . . . The caecum is generally normal in shape. Swelling is found on the whole surface of a mucous membrane. No bleeding is found in the content. Mucus is slightly yellowish and faded. A few white spot-like necroses or bleeding spots are found in a mucous membrane.

3, (+++) . . . The caecum is clearly withered and changed in shape, and is a little longer than the rectum. The content is quite abnormal and is often filled with coagulated blood or white-gray, cheese-like degenerated matter. The wall of the caecum is clearly swelled and easily broken and sometimes bleeding spots still remain. The diseased reaches a basis of the caecum but not the rectum.

4, (++++) . . . Withering and deformation of the caecum are remarkable. The caecum looks like a sausage in shape and is not longer than the rectum. The disease reaches almost one third or fourth of the rectum. The other points are the same as those described in item (3).

(iv) Feed Demand

The feed demand of each group tested was calculated from the average increase in weight and the total amount of feed ingested from the start to the end of the test (10 days).

$$\text{Feed demand} = \frac{\text{Amount of feed ingested}}{\text{Increase in weight}}$$

The results are given in Tables 2 and 3.

TABLE 2

| Group | | Amount of feed ingested (g) | Increase in weight (g) | Feed demand index |
|---|---|---|---|---|
| Control: | No infection No administration | 177.2 | 96.4 | 1.84 |
| Control: | Infection No administration | 177.4 | 87.0 | 2.04 |
| The antibiotic 76-11 | 50 ppm | 179.3 | 90.4 | 1.98 |
| The antibiotic 76-11 | 100 ppm | 174.4 | 80.4 | 2.17 |
| Salinomycin | 50 ppm | 170.6 | 91.8 | 1.86 |

TABLE 3

| Group | days | Control No infection No dosage | Control Infection[1] No dosage | The antibiotic 76-11 50 ppm | The antibiotic 76-11 100 ppm | Salinomycin 50 ppm |
|---|---|---|---|---|---|---|
| Change in weight (g) | −2 | 63.6 ± 1.56 | 63.0 ± 1.18 | 63.4 ± 0.98 | 63.4 ± 1.78 | 63.6 ± 1.08 |
| | 0 | 81.6 ± 3.12 | 79.6 ± 2.14 | 78.0 ± 2.98 | 79.6 ± 1.91 | 78.4 ± 1.21 |
| | 2 | 100.8 ± 4.42 | 100.6 ± 2.96 | 96.0 ± 4.00 | 96.0 ± 2.77 | 98.8 ± 1.52 |
| | 4 | 119.0 ± 4.76 | 122.2 ± 4.99 | 113.8 ± 4.99 | 113.4 ± 3.11 | 118.8 ± 1.96 |
| | 5 | 129.4 ± 5.20 | 125.6 ± 4.82 | 120.5 ± 6.41 | 121.6 ± 4.31 | 127.8 ± 2.65 |
| | 6 | 137.4 ± 5.14 | 133.4 ± 5.22 | 131.5 ± 6.33 | 127.4 ± 4.61 | 145.8 ± 2.96 |
| | 7 | 147.2 ± 5.40 | 141.6 ± 6.24 | 143.0 ± 7.29 | 136.2 ± 5.06 | 145.8 ± 4.00 |
| | 8 | 160.0 ± 5.74 | 150.0 ± 6.14 | 153.8 ± 7.76 | 143.8 ± 6.28 | 155.4 ± 4.74 |
| Increase in weight | | 78.4 | 70.4 | 75.8 | 64.2 | 77.0 |
| Relative increase in weight | | 100 | 89.8 | 96.7 | 81.9 | 98.2 |
| Bloody excre- | 4 | − | +++ | +++ | − | + |
| | 5 | − | ++ | + | − | ++ |

TABLE 3-continued

| Group | | Control No infection No dosage | Control Infection[1] No dosage | The antibiotic 76-11 50 ppm | The antibiotic 76-11 100 ppm | Salinomycin 50 ppm |
|---|---|---|---|---|---|---|
| ment[3] | 6 | — | ++ | + | — | + |
| and | 7 | — | + | — | — | — |
| death[4] | 8 | — | — | — | — | — |
| Survival | | 100 | 100 | 80 | 100 | 100 |
| The number of oocyst found in the intestinal canal | | 0 | $2,381 \times 10^7$ | $8.86 \times 10^6$ | $5.52 \times 10^5$ | $6.91 \times 10^6$ |
| Oocyst value | | 0 | 40 | 20 | 1 | 20 |
| Disease | ++++ | 0 | 3 | 1 | 0 | 1 |
| in the | +++ | 0 | 2 | 1 | 0 | 1 |
| intestinal | ++ | 0 | 0 | 3 | 0 | 0 |
| canal | + | 0 | 0 | 0 | 4 | 3 |
| | — | 5 | 0 | 0 | 1 | 0 |
| Disease value | | 0 | 36 | 26 | 8 | 20 |
| Anticoccidiosis index | | 200 | 114 | 131 | 173 | 158 |

[1]Infection: $5 \times 10^4$ Oocysts of *Eimeria tenella*/one chicken
[2]±: Standard error
[3]Degree of bloody excrement:
—; no
+; less than 10%
++; 10–30%
+++; 30–50%
++++; more than 50%
[4]Numerical values in parentheses show the number of dead chicken.

Thus, the administration of the anticoccidiosis agent of the present invention shows considerable improvements in bloody excrement, disease of the caecum and the number of oocyst detected in the intestinal canal as compared with the control group which was infected but not administered.

Further, it was found that the chickens to which the anticoccidiosis agent of the present invention were administered showed no symptoms of coccidiosis even after infected, that is, the growth of oocyst of *Eimeria tenella* was substantially inhibited and accordingly, the antibiotic 76-11 of the present invention was extremely useful for an anticoccidiosis agent.

The growth accelerating and feed efficiency increasing agent of the present invention will now be described with reference to the following Formulating and Test Examples.

Formulating Example 1

The antibiotic 76-11: 1%
Corn starch: 99%

Both the substances were pulverized and uniformly blended to give a premix containing 1% of the antibiotic 76-11.

Formulating Example 2

The antibiotic 76-11 (crude, purity 40%): 2.5%
Wheat bran: 97.5%

Both the substances were pulverized and uniformly blended to give a premix containing 1% of the antibiotic 76-11.

Formulating Example 3

1000 Grams of dry cells containing 0.96% of the antibiotic 76-11 is pulverized and is ready for use as a premix.

TEST EXAMPLE 2

Sixty cockerels (day-old) for broiler (Shaver Star Brow) were classified into three groups so that each group had the same average weight. Feeds to which the premix prepared according to Formulating Example 1 was added to contain the antibiotic 76-11 in the concentration of 25 ppm and 50 ppm, were fed to the first and the second groups respectively and, a feed to which the premix was not added, was fed to the third group, for seven weeks with continuity. Increase in weight and the total amount of feed ingested during this period were measured to calculate the feed demand index of each group. The results are shown in Table 4.

A feed for the former half was used from the beginning of the test to 21 days-old, afterward a feed for the latter half was used, both feeds for the former and the latter were those for broiler and contained no antibiotic, and the nutrient contents of each of the feeds are as follows:

| | For the former half use | For the latter half use |
|---|---|---|
| Crude protein | 23.4% | 20.4% |
| Crude fat | 5.5% | 6.1% |
| Crude fiber | 3.9% | 2.8% |
| Crude ash | 5.3% | 5.5% |
| Metabolizable energy | 3,020 Cal | 3,100 Cal |

TABLE 4

| Group | Additive | Weight (g) At the start | Weight (g) At the end | Increase in weight (g) | Feed ingested (g) | Feed demand index |
|---|---|---|---|---|---|---|
| 1. | The antibiotic 76-11 | 47 (100) | 1861 (105.9) | 1814 (106.1) | 3140 (99.8) | 1.731 (94.1) |

TABLE 4-continued

| Group | Additive | Weight (g) At the start | Weight (g) At the end | Increase in weight (g) | Feed ingested (g) | Feed demand index |
|---|---|---|---|---|---|---|
| 2. | The antibiotic 76-11 25 ppm | 47 (100) | 1879 (106.1) | 1832 (107.1) | 3120 (99.2) | 1.703 (92.6) |
| 3. | Control (No. addition) 50 ppm | 47 (100) | 1757 (100) | 1710 (100) | 3145 (100) | 1.839 (100) |

Note:
Numerical values in parentheses show the proportion (%) to Control.

Feed demand index = $\frac{\text{Amount of feed ingested}}{\text{Increase in weight}}$ As seen in the results described above, the administration of the antibiotic 76-11 in the concentration of 25 ppm and 50 ppm accelerated the growth by 6.1% and 7.1% respectively, and increased in the feed efficiency by 5.9% and 7.4% respectively.

It is found that the administration of the antibiotic 76-11 to herbivorous animals increases the ratio of propionic acid to acetic and butyric acids, which are formed within the rumen of the ruminant such as a cattle, a sheep and a goat, or within the large intestine of the animals having a single stomach such as a rabbit and a pig. On the other hand it is known that propionic acid is superior to acetic or butyric acids in utilization of volatile fatty acid as energy. Accordingly, it is believed that the administration of the antibiotic 76-11 accelerates the formation of propionic acid in a digestive organ, which accelerates the growth of animals and increases the feed efficiency. In addition, the administration of the antibiotic 76-11 can not only prevent bloat or ketosis which are frequently found in a beef cattle to which a large amount of concentrated feed is fed, but also cure the animals which have already suffered from such diseases. As an example of application to the ruminant, the following one is shown, wherein a feed to which the antibiotic 76-11 is uniformly added and blended is fed to a calf.

TEST EXAMPLE 3

Four castrated, Holstein calves weighing about 330 Kg (nine months-old) were divided into two groups. A feed to which the antibiotic 76-11 is added to be contained therein in the concentration of 30 ppm, was fed to the first group, while a feed to which the antibiotic 76-11 was not added, was fed to the second group, respectively for 16 weeks with continuity. The increase in weight and the total amount of feed ingested during this period were measured to calculate the feed demand index of each group. The results are shown in Table 5. The viscosity of and the content of volatile fatty acid in the rumen liquid collected by a catheter via nose just before and after the test were measured to calculate a molar ratio of propionic acid to acetic acid contained therein. The results are shown in Table 6.

A feed for a beef cattle "Kumiai New King Beef for the latter half" formulated by Zen-nō, Japan, which is freely ingested, and a dried rice plant (3 Kg/day. calf) were fed to the animals. The nutrient contents of "Kumiai New King Beef for the latter half" are as follows:

| Crude protein | 11.5% |
|---|---|
| Crude fat | 2.0% |
| Crude fiber | 9.0% |
| Crude ash | 9.0% |
| Digestible crude protein | 9.0% |
| Total digestible nutrient | 72.0% |

As seen from Table 5, the administration of the antibiotic 76-11 in the concentration of 30 ppm increased the feed demand index by 15%.

TABLE 5

| Group | Additive | Weight (kg) At the start | Weight (kg) At the end | Increase in weight (kg) | Feed ingested (kg) | Feed demand index |
|---|---|---|---|---|---|---|
| 1. | The antibiotic 76-11 30 ppm | 332 (99) | 457 (101) | 125 (108) | 880 (91) | 7.04 (85) |
| 2. | Control (No addition) | 335 (100) | 451 (100) | 116 (100) | 965 (100) | 8.32 (100) |

Note:
Numerical values in parentheses show the proportion (%) to Control.

TABLE 6

| | | Before the test | | After the test | |
|---|---|---|---|---|---|
| Group | Additive | Viscosity (CP) acid | Propionic acid/ Acetic | Viscosity (CP) acid | Propionic acid/ Acetic |
| 1. | The antibiotic 76-11 30 ppm | 4.1 (114) | 0.54 (98) | 3.2 (43) | 0.81 (180) |
| 2. | Control | 3.6 (100) | 0.55 (100) | 7.5 (100) | 0.45 (100) |

Note:
Numerical values in parentheses show the proportion (%) to Control.

As seen from Table 6, the administration of the antibiotic 76-11 in the concentration of 30 ppm inhibits the increase in the viscosity of the rumen liquid, which will be effective in preventing bloat. Further, the antibiotic 76-11 is believed to be effective in preventing ketosis, since the administration thereof increases the ratio of propionic acid produced.

The following shows, as an application to a herbivorous animal having a single stomach, an example in which a feed to which the antibiotic 76-11 is uniformly added and blended is fed to a piggy.

TEST EXAMPLE 4

Ten randrace piggies (two months-old) which are full-brother were classified into two groups of each five piggies so that each group had the same average weight and sex ratio. A feed to which the antibiotic 76-11 was added to be contained therein in the concentration of 50 ppm, was fed to the first group, while a feed to which the antibiotic 76-11 was not added, was fed to the second group respectively for ten weeks with continuity. The increase in weight and the total amount of feed ingested during this period were measured to calculate the feed demand index of each group. The results are shown in Table 7. In addition, the content of volatile fatty acid (VFA) in excrement was measured at the end of the test. The results are given in Table 8.

A feed for a piggy which has no antibiotic was used, of which formulation is as follows:
Cereals (corn, milo, wheat): 78%
Soybean oil cake: 13%
Fish meal: 5%
Others (Sodium chloride, Calcium carbonate, Calcium phosphate, etc.): 4%

TABLE 7

| Group | Additive | Weight (kg) At the start | Weight (kg) At the end | Increase in weight (kg) | Feed ingested (kg) | Feed demand index |
|---|---|---|---|---|---|---|
| 1. | The antibiotic 76-11 50 ppm | 14.07 (100) | 53.18 (112) | 39.11 (117) | 96.37 (106) | 2.464 (91) |
| 2. | Control (No. addition) | 14.08 (100) | 47.53 (100) | 33.45 (100) | 90.75 (100) | 2.713 (100) |

Note:
Numerical values in parentheses show the proportion (%) to Control.

As seen from Table 7, the administration of the antibiotic 76-11 in the concentration of 50 ppm accelerated the growth by 17% and increased the feed demand index by 9%.

TABLE 8

| Group | Additive | Total amount of VFA (mmol/g) | Molar ratios of each fatty acid to the total amount of VFA Propionic acid | Acetic acid | Butyric acid |
|---|---|---|---|---|---|
| 1. | The antibiotic 76-11 50 ppm | 0.176 (96) | 32.7 (11.8) | 39.9 (96) | 15.3 (84) |
| 2. | Control | 0.183 (100) | 27.8 (100) | 41.7 (100) | 18.3 (100) |

Note:
Numerical values in parentheses show the proportion (%) to Control.

It is known that the amount of volatile fatty acid (VFA) absorbed by the intestinal canal of a pig is not changed according to the kind of the fatty acid. Accordingly, it is believed that the increase in the content of propionic acid contained in excrement, by the administration of the antibiotic 76-11 in the concentration of 50 ppm, shows the increase in the production of propionic acid in the intestinal canal.

What we claim is:

1. The antibiotic 76-11 having the following physicochemical and biological properties:
   (1) Elemental Analysis:
      Free acid: C; 62.61%, H; 8.27%, N; 0%
      Na salt: C; 60.57%, H; 8.04%, N; 0%,
   The antibiotic containing no element other than carbon, hydrogen and oxygen;
   (2) Molecular Weight:
      843 (measured by a titration method)
      873 (measured by FD mass spectrum method)
   (3) Melting Point:
      Free acid: 108°–112° C.
      Na salt: 210°–212° C. (Decomposed)
   (4) Specific Rotatory Power:
      $[\alpha]_D^{25} + 36.6°$ (C=0.382, in chloroform solution)
   (5) Ultraviolet Absorption Spectrum:
      The maximum absorption bands;

In MeOH and HCl—MeOH:

$\lambda_{max} = 217$ m$\mu$ ($E_{1\,cm}^{1\%}$ 303)

262 m$\mu$ ($E_{1\,cm}^{1\%}$ 182)

301 m$\mu$ ($E_{1\,cm}^{1\%}$ 68)

In alkaline MeOH:

$\lambda_{max} = 260$ m$\mu$ ($E_{1\,cm}^{1\%}$ 87)

308 m$\mu$ ($E_{1\,cm}^{1\%}$ 50)

(6) Infrared Absorption Spectrum:
      Main specific absorption bands in KBr plate:
      Free acid: 3450, 2960, 1720, 1640, 1610, 1578, 1446, 1380, 1315, 1292, 1250, 1209, 1151, 1100, 1035, 975, 940 cm$^{-1}$
      Na salt: 3390, 2960, 1718, 1640, 1609, 1578, 1450, 1380, 1340, 1316, 1250, 1197, 1152, 1108, 1092, 1060, 1040, 1002, 980, 930 cm$^{-1}$
   (7) Solvent Solubility:
      Easily soluble in benzene, chloroform, ethyl acetate and acetone, soluble in methanol, ethanol and dimethylformamide, and hardly soluble in water and hexane
   (8) Coloring Reactions:
      Positive to potassium permanganate reaction but negative to periodic acid-benzidine reaction
   (9) Basicity, Acidity or Neutrality:
      Acidic substance, pKa' 4.6 (in 66.7% dioxane)
   (10) Color:
      Colorless crystal
   (11) Antimicrobial Activity:
      Growth inhibition against Gram positive coccus, bacillus and acid-fast bacteria reveals in the concentration of 0.4 mcg/ml.

2. A process for producing the antibiotic 76-11 defined in claim 1 which comprises the following steps:
   (a) culturing Actinomadura Sp. 76-11 (FERM BP-83) in a culture medium at a pH in the range of about 4 to 9 at a temperature of about 25° to 35° C., and for a time sufficient to obtain a maximum production of the antibiotic 76-11 in the culture medium with aeration and agitation;

(b) centrifuging the culture medium to separate the cells therefrom;

(c) extracting the supernatant obtained and the cells with solvents respectively;

(d) combining the extracts obtained and concentrating the combined extract to obtain a concentrate;

(e) subjecting the concentrate thus obtained to adsorption chromatography;

(f) eluting the substances adsorbed in step (e) with solvents to obtain an active fraction containing the antibiotic 76-11; and (g) purifying the active fraction of antibiotic 76-11 by concentration and crystallization.

3. A method for prevention and cure of coccidiosis of domestic fowls which comprises orally administering the amount of 5 to 200 ppm of the antibiotic 76-11 defined in claim 1 and feed materials to the domestic fowls.

4. A method for prevention and cure of coccidiosis of domestic fowls according to claim 3, wherein the amount of the antibiotic 76-11 defined in claim 1 is 10 to 100 ppm.

5. A method for accelerating the growth of domestic animals and fowls and increasing the feed efficiency thereof which comprises orally administering the amount of 1 to 200 ppm of the antibiotic 76-11 defined in claim 1 and physiologically acceptable solid or liquid carriers to the animals and fowls.

6. A method for accelerating the growth of domestic animals and fowls and increasing the feed efficiency thereof according to claim 5, wherein the amount of the antibiotic 76-11 defined in claim 1 is 2 to 100 ppm.

7. A feed composition comprising 1–200 ppm of the antibiotic 76-11 defined in claim 1 and at least one physiologically acceptable solid or liquid carrier.

* * * * *